United States Patent [19]
Caillot et al.

[11] Patent Number: 5,801,150
[45] Date of Patent: Sep. 1, 1998

[54] AMINOPYRI(MI)DINE DERIVATIVES COMBINED WITH AMINO ACIDS, AND PHARMACOLOGICAL ACTIVITIES THEREOF

[76] Inventors: Jean-Luc Caillot, 32 rue du Moulin, 67205 Oberhuasbergen; Louis Jung, 205 route d'Oberhausbergen, 67200 Strasbourg; Minjie Zhao, 119 route de Colmar, 67100 Strasbourg, all of France

[21] Appl. No.: 571,832

[22] PCT Filed: Jun. 22, 1994

[86] PCT No.: PCT/FR94/00753

§ 371 Date: Jul. 2, 1996

§ 102(e) Date: Jul. 2, 1996

[87] PCT Pub. No.: WO95/00495

PCT Pub. Date: Jan. 5, 1995

[30] Foreign Application Priority Data

Jun. 23, 1993 [FR] France .................. 93 07821

[51] Int. Cl.⁶ .................. A61K 38/00; C07K 5/00
[52] U.S. Cl. .................. 514/18; 514/19; 514/256; 514/275; 514/774; 530/331; 530/345
[58] Field of Search .................. 530/345, 331; 514/256, 275, 774, 18, 19

[56] References Cited

U.S. PATENT DOCUMENTS

| | | | |
|---|---|---|---|
| 4,528,135 | 7/1985 | Henninger et al. | 260/245.2 |
| 4,959,475 | 9/1990 | Mills et al. | 544/324 |
| 5,124,154 | 6/1992 | Babcock et al. | 424/427 |
| 5,328,913 | 7/1994 | Murad et al. | 514/275 |

FOREIGN PATENT DOCUMENTS

| | | |
|---|---|---|
| 8600616 | 1/1986 | European Pat. Off. . |
| 2175901 | 12/1986 | United Kingdom . |

OTHER PUBLICATIONS

R. B. Merrifield, Science vol. 150 Oct. '65 pp. 178–185.
Chemical Abstract No. 1988: 515976; Bennett et al., J. Bioact. Compat. Polym. (1988) 3(1) pp. 44–52.
Brunozzzi et al, Acta Therapeutica vol. 12 (1986) pp. 373–381.

*Primary Examiner*—Douglas W. Robinson
*Assistant Examiner*—Bennett Celsa
*Attorney, Agent, or Firm*—Young & Thompson

[57] ABSTRACT

Synthetic compounds combining sulphur-containing or sulphur-free amino acids with aminopyrimidine and aminopyridine derivatives, as well as mineral or organic acid addition salts produced in the presence of an amino grouping, were synthesized. Non-sulphur amino acids such as glutamic acid, pyroglutamic acid, tyrosine, histidine and arginine, and sulphur amino acids such as methionine, cysteine, S-methyl-cysteine and cystine, were attached to minoxidil to give monosubstituted and disubstituted derivatives. The amides with a pyrimidine or pyridine structure coupled to an amide structure in which the carbonyl is from sulphur-containing or sulphur-free amino acid have the properties of; (1) excellent adhesion to the skin, particularly the epidermis; (2) capturing free radicals, in particular the superoxide anion and the hydroxyl radical; (3) selectively relaxing smooth muscle fibers; and (4) in vitro and in vivo keratinocyte growth, hair growth in humans, and fresh and accelerated fur growth in animals.

16 Claims, 1 Drawing Sheet

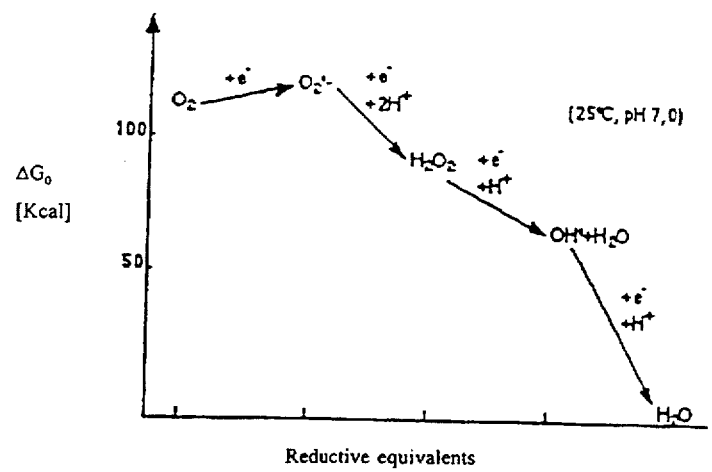
FIG. 1 Study of the capture of superoxide anion and of hydroxyl radicals ($O_2^{\circ-}$ and $OH^\circ$).

AMINOPYRI(MI)DINE DERIVATIVES COMBINED WITH AMINO ACIDS, AND PHARMACOLOGICAL ACTIVITIES THEREOF

This application is a 371 of PCT/FR94/00753 filed Jun. 22, 1994.

BACKGROUND OF THE INVENTION

1. Field of the Invention

The invention has for its object new synthetic compounds combining sulfur-containing or sulfur-free amino acids with aminopyrimidine and aminopyridine derivatives, as well as their addition salts with mineral or organic acids in the presence of amino groups, their processes for preparation, their pharmacological activities and the pharmaceutical compositions containing them.

2. Description of the Related Art

On the other hand, the salification of minoxidil by amino acids is disclosed by British patent 2 175 901. In this patent, a salt is formed between 5-oxoproline and the 2,4-diamino-6-piperidinopyrimidine-3-oxide (minoxidil).

Minoxidil is also disclosed in a patent WO-A-8 600 616 corresponding to an associative synthesis with alkoxy or alkoxycarbonyl compounds different from the amidic structures of the present claims.

At present, the minoxidil molecule is the base for our study and is known for its following properties:

- it is used in the treatment of arterial hypertension by reduction of the arterial pressure resulting from selective relaxation of the smooth muscle fibers of the peripheral arteries.
- on the other hand, minoxidil applied topically stimulates the in vitro and in vivo growth of keratinocytes, and the growth of hair, in certain subjects having androgenic alopecy. The appearance of this phenomenon takes place after about four months (or more) of use of the product and varies as a function of the subjects. Minoxidil, when applied topically, is only slightly absorbed: an average quantity of 1.4% (for values ranging from 0.3 to 4.5%) of the applied dose reaches the blood stream.

The mechanism in the framework of fresh growth of hair will be based on the vasodilatory properties of the peripheral arteries of the hair-bearing skin. However, regrowth of hair requires prolonged treatment; the hairs formed are fragile and in particular the molecular weight of the keratines formed is less than that of normal strands.

SUMMARY OF THE INVENTION

The new compounds of the invention have a power of capturing free radicals which is higher, acting as such, and are of vasodilatory activity origin; they have a cutaneous penetration and retention in the skin which is substantially greater.

The original compounds disclosed for the first time and whose invention is claimed here, are aminopyrimidine and aminopyridine derivatives of formulas 1 to 4:

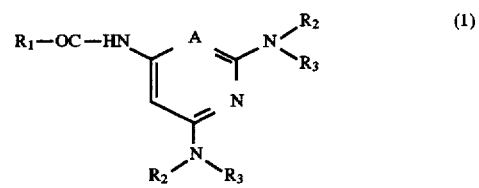
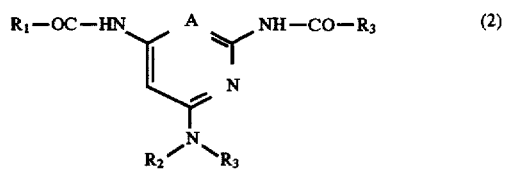
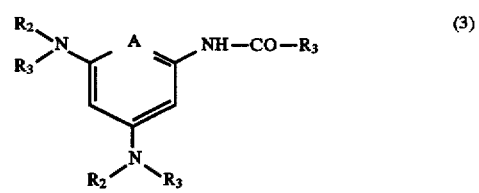
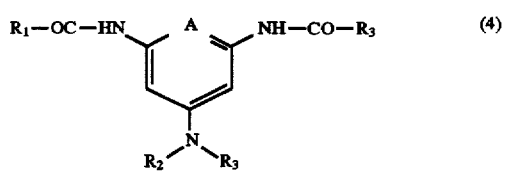

wherein A represents either a nitrogen atom or an N-oxide group of the structure $N^+$—$O$—$^-$.

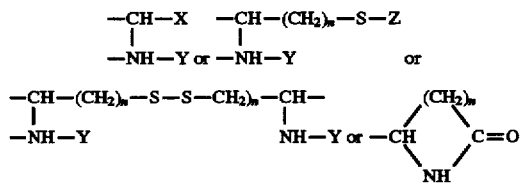

wherein X and Y represent hydrogen, a linear or branched alkyl group, possibly hydroxylated, an aryl group, an alkylaryl group, an amino alkyl group, an amino aryl group, a carboxyalkyl group, or a carboxyaryl group.

Z represent hydrogen, an alkyl group, or an aryl group, n being 1 to 6, preferably 1 or 2.

$R_2$ and $R_3$ represent hydrogen, a linear or branched alkyl group, possibly hydroxylated, an aryl group, an amino alkyl group, an amino aryl group, or a heterocyclic group;

—CO—$R_1$ represents a peptide structure comprising two or several amino acids whose terminal or branched acid or amine functions can be free or combined with ester or amide groups.

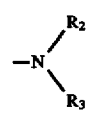

represents a cyclic structure either

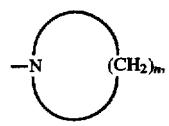

n being preferably 4 to 6 or

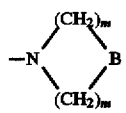

wherein m is 2, B is a heteroatom, O, NH or amino substituted with a linear, branched or optionally hydroxylated alkyl group, or an aryl group, the amino function —NH—Y is an amine, Y being hydrogen, either in the form of mineral or organic salts, or in the form of an amide, Y having the structure CO—$R_4$, $R_4$ being identical to $R_2$ excluding hydrogen.

These amides derive from monoamino, diamino and triamino-pyrimidines and from monoamino, diamino and triamino pyridines.

They result from the combination of either an aminopyrimidine or an aminopyridine and amino acids or sulfur-free peptides, such as for example glutamic acid, pyroglutamic acid, tyrosine, histidine, arginine, citrulline or sulfur-containing amino acids or peptides such as methionine, cysteine, S-methylcysteine, S-benzylcysteine, cystine, glutathion, or oxidized glutathion.

As an example could be cited the combination of minoxidil and amino acids or sulfur-free peptides, such as for example glutamic acid, pyroglutamic acid, tyrosine, histidine, arginine, citrulline or sulfur-containing amino acids or peptides such as methionine, cysteine, S-methylcysteine, S-benzylcysteine, cystine, glutathion or oxidized glutathion.

The lazaroides, with aminated substitution at the 6-position of 2,4-diaminopyrimidine (amine in the form of a primary aromatic amine) being a piperazine substituted by a 21-aminosteroid which is not a glucocorticoid, can replace minoxidil.

The amides according to formulas 1 to 4 are obtained by combination of a diaminopyrimidine and a diaminopyridine and a carboxyl function of an amino acid or peptide, leading to a monosubstituted derivative or to a disubstituted derivative. As diaminopyrimidine can be used minoxidil, resulting in a monosubstituted derivative or a disubstituted derivative.

These amides having a pyrimidine or pyridine structure coupled to an amide structure, whose carbonyl is of amino acid or sulfur-containing peptide or sulfur-free peptide origin, have several properties:

1) good adhesion to the skin, particularly at the epidermis.
2) capture of free radicals, particularly the capture of the superoxide anion and of the hydroxyl radical.
3) a reduction of the arterial pressure resulting from a selective relaxation of the smooth muscular fibers and the peripheral arteries.
4) the in vitro and in vivo growth of keratinocytes, and the growth of hairs on humans and the fresh growth and acceleration of the growth of animal hair.

The amides that have salified aminoalkyl or aminoaryl groups, for example in the form of chlorohydrate, or organic or mineral salts of a free carboxylic function, are soluble in water, the others being somewhat liposoluble.

In the present description, the term "alkyl" designates aliphatic hydrocarbon groups containing 1 to 12 carbon atoms, straight chain or branched chain. Lower alkyl groups are preferred, which is to say alkyl groups containing 1 to 4 carbon atoms.

The term "aryl" designates nonheterocyclic aromatic groups of the type of phenyl, phenol, benzyl and higher homologs, substituted or not, as well as heterocyclic aromatic groups having 2 to 7 carbon atoms in the aromatic cycle, and 1 to 4 heteroatoms which can be oxygen, nitrogen, sulfur, or of the type of furan, pyridine or oxazole.

The term "aminoalkyl" designates aliphatic hydrocarbon groups containing 1 to 12 carbon atoms and 1 to 3 nitrogen atoms, straight chain or branched chain, groups containing 1 to 4 carbon atoms and 1 nitrogen atom are preferred.

The term "aminoaryl" designates nitrogen containing substituents with aromatic cycles.

The term "mineral salt" designates preferably a salt either of sodium, or of potassium, or of calcium.

The term "organic salt" preferably designates a salt, obtained by the action of a primary or secondary or tertiary amine on the carboxyl group: preferred are either ethanolamine salt, or a piperidine salt, or a pyrrolidine salt, or a salt of pyridine or their derivatives.

The term "carboxyalkyl" designates a hydrocarbon group ending in a carboxylic function.

The term "carboaryl" designates an aromatic group with a carboxylic substituent.

The term "amino acid" designates α-alanine, arginine, asparagine, aspartic acid, cysteine, cystine, glutamic acid, glutamine, glycocol, histidine, δ-hydroxylysine, hydroxyproline, leucine, isoleucine, lysine, methionine, norleucine, phenylalanine, proline, serine, threonine, tryptophane, tyrosine, valine, β-alanine, n-butyric α-amino acid, n-butyric γ-amino acid, β-amino isobutyric acid, δ-amino levulinic acid, carbamyl-aspartic acid, citrulline, creatinine, ornithine or taurine.

BRIEF DESCRIPTION OF THE DRAWINGS

FIG. 1 describes the formation of different reactive species of oxygen.

DETAILED DESCRIPTION OF THE PREFERRED EMBODIMENT

The preparation of the amides comprises causing to react an N-substituted amino acid, for example N-acetylated, with the amino group or groups of an aminopyrimidine and of an aminopyridine by means of a peptide synthesis reaction, for example dicyclohexylcarbodiimide. The selected examples are those of minoxidil with N-acetyl, D,L-methionine and pyroglutanic acid.

monosubstitued derivative

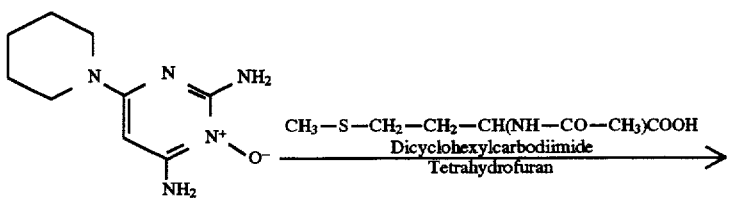

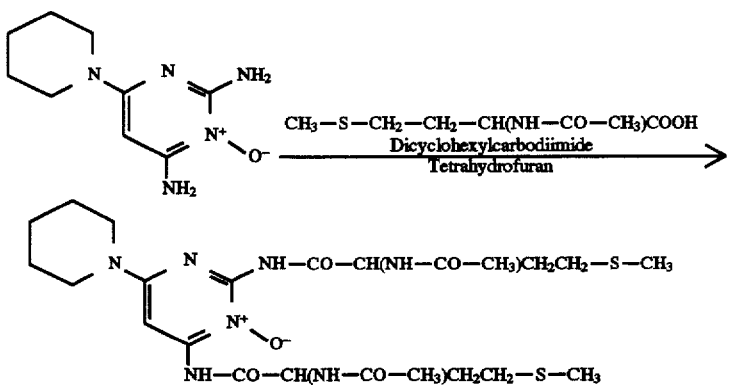

The two derivatives are separated by chromatography.

Combined synthesis of minoxidil and pyroglutamic acid

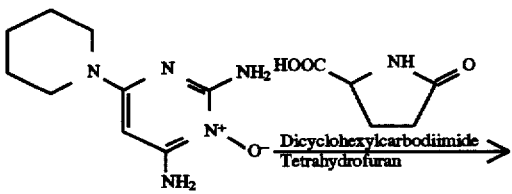

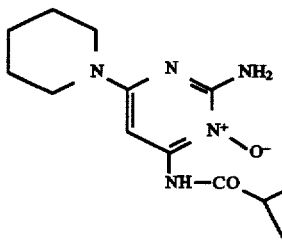

Minoxidil monosubstituted and disubstituted with N-acetyl-D,L-methionine

In a 100 ml flask with a ground stopper, is dissolved 0.5 g of minoxidil (0.0024 mole) in 40 ml of tetrahydrofuran, for 5 mins. with agitation. 0.59 g of dicyclohexylcarbodiimide (0.0029 mole) is added, then 0.5 g of N-acetyl-D,L-methionine (0.0026 mole). It is agitated at ambient temperature for one hour under an atmosphere of argon.

The reaction mixture is filtered, then the filtrate is evaporated under reduced pressure.

The residue is purified by chromatography on silica gel. The monosubstituted and disubstituted minoxidils are eluted by a mixture MeOH/CH$_2$Cl$_2$ (5/95) to obtain 0.20 g of monosubstituted minoxidil and 0.14 g of disubstituted minoxidil.

The yields are respectively 20 and 10.5%.

Analyses:

Monosubstituted minoxidil:

melting point 138° C.

CCM (CH$_3$OH:CH$_2$Cl$_2$-10/90) Rf: 0.72

1H-RMN (DMSO):=1.52 (m; 6H; CH$_2$—CH$_2$—CH$_2$—CH$_2$—N); 1.91 (s; 3H; CO—CH$_3$); 2.05 (s; 3H; S—CH$_3$); 2.07 (m; 2H; CH$_2$—CH$_2$—S—CH$_3$); 2.50 (m; 2H; CH$_2$—S—CH$_3$); 3.49 (m; 4H; CH$_2$—N—CH$_2$); 4.41 (m; 1H; CO—CH—NH); 6.9 (s; 1H; Harom.); 7.19 (s wide; 2H; NH$_2$); 8.58 (d; 1H; NH—CO—CH$_3$); 10.94 (s; 1H; φ—NH—CO).

Disubstituted monoxidil:

melting point 228° C.

CCM (CH$_3$OH:CH$_2$Cl$_2$-10/90) Rf: 0.94

1H-RMN (DMSO):=1.56 (m; 6H; CH$_2$—CH$_2$—CH$_2$—CH$_2$—N); 1.91 (s; 6H; CO—CH$_3$); 2.01 (m; 4H; CH$_2$—CH$_2$—S—CH$_3$); 2.05 (s; 6H; S—CH$_3$); 2.50 (m; 4H; CH$_2$—S—CH$_3$); 3.56 (m; 4H; CH$_2$—N—CH$_2$); 4.58 (m; 2H; CO—CH—NH); 7.25(s; 1H; Harom.); 8.50 (d; 1H; NH—CO—CH$_3$); 8.53 (d; 1H; NH—CO—CH$_3$); 10.53 (s; 1H; φ—NH—CO); 10.64 (s; 1H; φ—NH—CO).

Monoxidil monosubstituted with pyroglutamic acid

In a 100 ml flask with a ground stopper, 0.5 g of minoxidil (0.0024 mole) is introduced into 40 ml of tetrahydrofuran and stirred for 5 mins.

0.59 g of dicyclohexylcarbodiimide (0.0029 mole) is added, then 0.32 g of pyroglutamic acid (0.0025 mole).

After 1 hour the mixture is filtered. The filtrate is evaporated under reduced pressure. The residue is recovered with a 1N hydrochloric acid solution and extracted with dichloromethane. The aqueous phase thus obtained, after addition of a sufficient quantity of 15% ammonia, is extracted with dichloromethane. This solution is washed several times with water. The organic phase is recovered, dried on magnesium sulfate and evaporated under reduced pressure. The residue obtained is suspended in hot diisopropyl oxide, then is hot filtered. There is recovered from the filter 0.25 g of monosubstituted minoxidil in the form of a white powder.

The yield is 32%.
Analyses:
Melting point: 232° C.
CCM (CH$_3$OH:CH$_2$Cl$_2$-10/90) Rf: 0.45
1H-RMN (DMSO):=1.14 (m; 2H; C$\underline{H}_2$—CH$_2$—CO); 1.57 (m; 6H; C$\underline{H}_2$—C$\underline{H}_2$—C$\underline{H}_2$—CH$_2$—N); 2.17 (m; 2H; CH$_2$—C$\underline{H}_2$—CO); 3.32 (m; 4H; C$\underline{H}_2$—N—C$\underline{H}_2$); 4.42 (m; 1H; C$\underline{H}$—NH—CO); 5.56 (d; 1H; N$\underline{H}$—CO—CH$_2$); 6.95 (s; 1H; $\underline{H}$arom.); 7.20 (s wide; 2H; N$\underline{H}_2$); 8.11 (s; 1H; φ—N$\underline{H}$—CO).

It is also envisaged to cause to react an N-substituted amino acid, for example N-acetylated, on the amino group or groups of an N-oxide aminopyrimidine and of an N-oxide aminopyridine by means of a peptide synthesis reaction, for example dicyclohexylcarbodiimide.

It is possible to transform an N-oxide aminopyrimidine derivative and an N-oxide aminopyridine derivative into its corresponding amine and to cause it to react with zinc in hydrochloric medium in an ethanol solution.

Reduced minoxidil

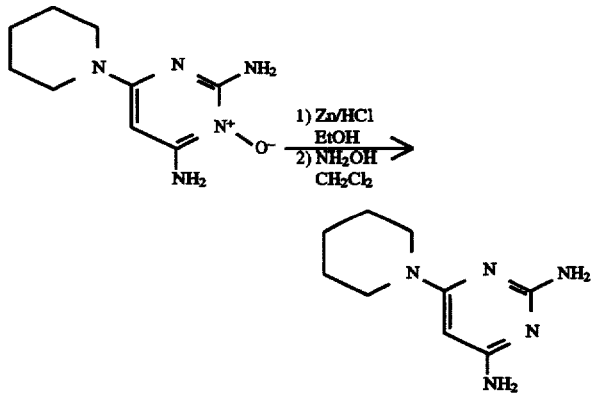

To a solution of 0.5 g of minoxidil (0.0024 mole) in 15 ml of 95% ethanol, there is added 15 ml of a mixture of concentrated hydrochloric acid and distilled water (50/50).

There is fractionally added thereto 1.569 g of zinc powder (0.024 mole). This is stirred for 30 mins. and the excess of zinc is filtered off. The alcohol is evaporated under reduced pressure and distilled water is added, then it is rendered alkaline with a large excess of concentrated ammonium, before extracting the dichloromethane. The organic phase is washed with water and dried on magnesium sulfate.

After evaporation of the solvent under reduced pressure, there is obtained an oily residue which is crystallized in dioxypropyl oxide. A recrystallization in ethanol gives 0.14 g of reduced monoxidil.

The yield is 26%.
Analysis:
Melting point: 118° C.
CCM (CH$_3$OH:CH$_2$Cl$_2$-10/90) Rf: 0.40
1H-RMN (CDCl3):=1.56 (m; 6H; C$\underline{H}_2$—C$\underline{H}_2$—CH$_2$CH$_2$—N); 3.49 (m; 4H; C$\underline{H}_2$—N—C$\underline{H}_2$); 4.29 (s wide; 2H; N$\underline{H}_2$); 4.48 (s wide; 2H; N$\underline{H}_2$); 5.15 (s; 1H; $\underline{H}$arom.)

The aminopyrimidine N-oxide and aminopyridine N-oxide amides can be prepared by causing to react perhydrol in an ethanol solution.

The novel products described can be used as medication by any route, for example as hypotensive agents in combination with excipients, suitably in the form of tablets or capsules for example.

They can also be used in dermopharmaceutical compositions or cosmetological compositions in combination with a suitable vehicle, solution, emulsion, spray for example, all being for application to the surface of human skin.

The amides of formulae 1-4 preferably represent one of the following compounds:
amide of 2,4-diamino-6-piperidinopyrimidine-3-oxide and N-acetyl-D,L-methionine (formula 1);
diamide of 2,4-diamino-6-piperidinopyrimidine-3-oxide and N-acetyl-D,L-methionine (formula 2);
amide of 2,6-diamino-4-piperidinopyridine-1-oxide and N-acetyl-D,L-methionine (formula 3);
diamide of 2,6-diamno-4-piperidinopyridine-1-oxide and N-acetyl-D,L-methionine (formula 4);
amide of 2,4-diamino-6-piperidinopyrimidine-3-oxide and D,L-methionine (formula 1);
diamide of 2,4-diamino-6-piperidinopyrimidine-3-oxide and D,L-methionine (formula 2);
amide of 2,6-diamino-4-piperidinopyridine-1-oxide and D,L-methionine (formula 3);
diamide of 2,6-diamino-4-piperidinopyridine-1-oxide and D,L-methionine (formula 4);
amide of 2,4-diamino-6-piperidinopyrimidine-3-oxide and cysteine (formula 1);
diamide of 2,4-diamino-6-piperidinopyrimidine-3-oxide and cysteine (formula 2);
amide of 2,6-diamno-4-piperidinopyridine-1-oxide and cysteine (formula 3);
diamide of 2,6-diamino-4-piperidinopyridine-1-oxide and cysteine (formula 4);
amide of 2,4-diamino-6-piperidinopyrimidine-3-oxide and cystine (formula 1);
diamide of 2,4-diamino-6-piperidinopyrimidine-3-oxide and cystine (formula 2);
amide of 2,6-diamno-4-piperidinopyridine-1-oxide and cystine (formula 3);
diamide of 2,6-diamino-4-piperidinopyridine-1-oxide and cystine (formula 4);
amide of 2,4-diamino-6-piperidinopyrimidine-3-oxide and pyroglutamic acid (formula 1);
diamide of 2,4-diamino-6-piperidinopyrimidine-3-oxide and pyroglutamic acid (formula 2);
amide of 2,6-diamino-4-piperidinopyridine-1-oxide pyroglutamic acid (formula 3);
diamide of 2,6-diamino-4-piperidinopyridine-1-oxide pyroglutamic acid (formula 4);
amide of 2,4-diamino-6-piperidinopyrimidine and N-acetyl-D,L-methionine (formula 1);
diamide of 2,4-diamino-6-piperidinopyrimidine and N-acetyl-D,L-methionine (formula 2);
amide of 2,6-diamino-4-piperidinopyridine and N-acetyl-D, L-methionine (formula 3);
diamine of 2,6-diamino-4-piperidinopyridine and N-acetyl-D,L-methionine (formula 4);

amide of 2,4-diamino-6-piperidinopyridine and D,L-methionine (formula 1);

diamide of 2,4-diamino-6-piperidinopyrimidine and D,L-methionine (formula 2);

amide of 2,6-diamino-4-piperidinopyridine and D,L-methionine (formula 3);

diamide of 2,6-diamino-4-piperidinopyridine and D,L-methionine (formula 4);

amide of 2,4-diamino-6-piperidinopyrimidine and cysteine (formula 1);

diamide of 2,4-diamino-6-piperidinopyrimidine and cysteine (formula 2);

amide of 2,6-diamino-4-piperidinopyridine and cysteine (formula 3);

diamide of 2,6-diamino-4-piperidinopyridine and cysteine (formula 4);

amide of 2,4-diamino-6-piperidinopyrimidine and cystine (formula 1);

diamide of 2,4-diamino-6-piperidinopyrimidine and cystine (formula 2);

amide of 2,6-diamino-4-piperidinopyridine and cystine (formula 3);

diamide of 2,6-diamino-4-piperidinopyridine and cystine (formula 4);

amide of 2,4-diamino-6-piperidinopyrimidine pyroglutamic acid (formula 1);

diamide 2,4-diamino-6-piperidinopyrimidine pyroglutamic acid (formula 2);

amide of 2,6-diamino-4-piperidinopyridine and pyroglutamic acid (formula 3);

diamide of 2,6-diamino-4-piperidinopyridine and pyroglutamic acid (formula 4).

CAPTURE OF FREE RADICALS (FR)

The methods used can produce selectively a chosen type of FR (superoxide anion or hydroxyl radical). The detector must be able to detect proportionally all the FR formed.

Overall scheme of the quantification of the capture of free radicals

Step of production and detection of FR: the radicular source supplies the free radical which will react with a detector to form a modified detector. This latter could be quantified directly or after interaction with an analytic reaction complement by spectrophotometric analysis.

Determination either of the percent of sensing or of the speed constant of the sensor: a sensor enters into competition with the detector to form a modified sensor. There is obtained a reduction of the quantity of the modified detector which gives us, after mathematical analysis, either the speed constant of the reaction of the sensor with the radical, or the percentage of sensing of this radical by the sensor.

Sensing superoxide anion

The methodology is the auto-oxidation of adrenaline: adrenaline plays the double role of producing superoxide anion and serving as a detector. Adrenaline which is stable at acid pH, oxidizes spontaneously at alkaline pH. This complex reaction gives after several steps, adrenochrome. The superoxide anion participates in it as an oxidizing agent. The formation of adrenochrome is followed at 480 nm.

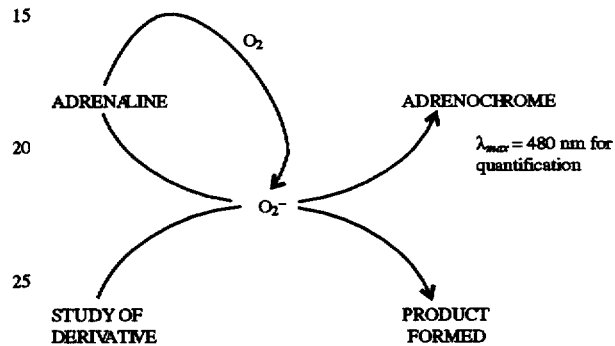

Capture of the superoxide anion: oxidation of adrenaline

The reaction medium is constituted by 3.1 ml of sodium carbonate (0.05M) at pH 10.2 containing EDTA (0.1 mM). The oxidation reaction is initiated by the addition of 0.2 ml of adrenaline (0.01M, in 0.02N HCl). The formation of adrenochrome is followed for 2 mins. at 480 nm. The compounds to be studied are added with the aide of 0.02 ml of DMSO, before the addition of adrenaline.

The capacity of the substances to sense the superoxide anion is expressed in terms of percentage of inhibition (%I).

$$\% I = \frac{A_0 - A}{A_0} \times 100\%$$

$A_0$ and $A$ are respectively the absorbance of the detector modified in the absence and in the presence of the derivative studied.

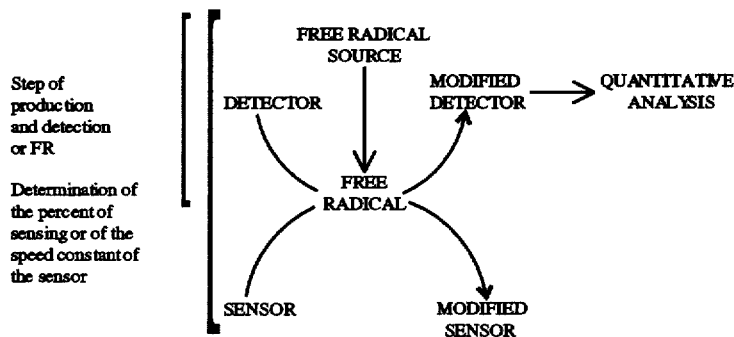

| % inhibition of superoxide-dismutase (SOD) | | | | | |
|---|---|---|---|---|---|
| SOD (μg/ml) | 33.3 | 83.3 | 133.6 | 166.6 | 217.1 |
| % of inhibition | 20 | 37.93 | 48.39 | 60.71 | 66.67 |

| % inhibition of cysteine | | | | | | | | | |
|---|---|---|---|---|---|---|---|---|---|
| cysteine (mM) | 0.005 | 0.008 | 0.01 | 0.02 | 0.03 | 0.04 | 0.05 | 0.06 | 0.07 |
| % of inhibition | 6.52 | 8.58 | 9.61 | 221.12 | 31.72 | 34.45 | 46.71 | 51.93 | 57.17 |

The method of production and of detection of the superoxide anion is validated by SOD, which is the specific enzyme of the degradation of the superoxide anion.

Apart from SOD, cysteine is known as the most reactive with respect to the superoxide anion.

The concentration at which there is obtained 50% inhibition is of the order of 0.051 mM for cysteine, 0.25 mM for minoxidil and 0.67 mM for the compound disubstituted with N-acetyl-methionine. The monosubstituted compound at a concentration of 0.6 mM has an inhibition of 32%.

At a concentration of 0.6 mM of N-acetyl-methionine, we have not observed activity. It is only at 2 mM that we observe an inhibition of 10%.

The examples which were the object of this study show a sensor power of the superoxide anion identical to that of minoxidil, but their interest arises from the fact of cutaneous penetration which is greater by more than ten times.

Capture of the hydroxyl radical

The Fenton reaction, the catalytic decomposition of hydrogen peroxide ($H_2O_2$) by the action of $Fe^{2+}$, has been used to produce the hydroxyl radical $$Fe^{2+} + H_2O_2 \rightarrow Fe^{3+} + OH^- + OH°$$

As the hydroxyl radical has a very short life, it is necessary to use an indirect method to detect it.

Because of its widespread use, the test of oxidative degradation of deoxyribose has been selected for our study. The hydroxyl radical generated by the Fenton reaction degrades the deoxyribose and produces malonaldehyde which forms a colored complex with thiobarbituric acid. This complex is quantified by colorimetry at a wavelength of 532 nm. This methodology can be represented by the following scheme:

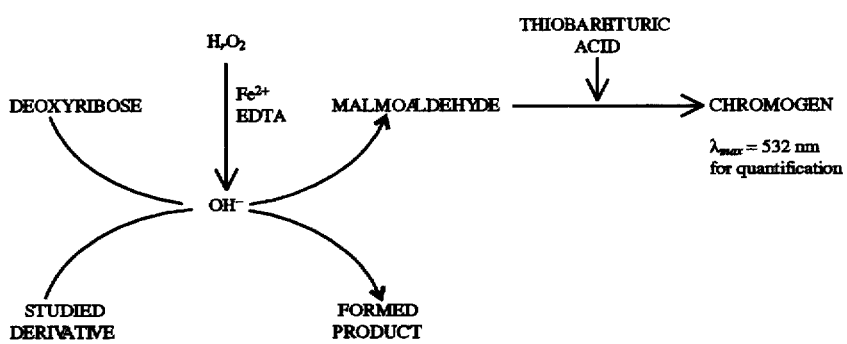

| -continued | | | | | | | | |
|---|---|---|---|---|---|---|---|---|
| % of inhibition of minoxidil, of monosubstituted and disubstituted derivatives of N-acetyl-methionine | | | | | | | | |
| Derivatives Conc. (mM) | 0.05 | 0.1 | 0.2 | 0.3 | 0.4 | 0.5 | 0.6 | 0.7 |
| Minoxidil | 11.71 | 25.62 | 41.86 | 57.20 | — | 74.12 | 82.70 | — |
| Monosubstituted (N-acetyl-methionine) | — | 7.57 | 14.49 | 19.38 | 25.71 | 27.17 | 32.01 | — |
| Disubstituted (N-acetyl-methionine) | — | 10.56 | 15.62 | 25.99 | 30.77 | 38.71 | 43.75 | 53.22 |

In the literature, the results are presented most often in percentage of inhibition and compared with known sensors (mannitol, for example) but each possible time, speed constants are used.

The speed constants have been determined by using the Halliwell method with modifications. The final kinematic equation is the following $$\frac{1}{A} = \frac{1}{A_0} \times 1 + \frac{k_s \cdot S}{k_d \cdot D + k_x}$$

A and $A_0$: absorbances at 532 nm of the complex in the presence and in the absence of the studied derivative.

$k_S$ and $k_d$: speed constants of the reaction of OH° with the studied derivative and deoxyribose.

S and D: concentrations of studied derivative and of deoxyribose.

$k_x$: term representing the reactivity of the radical OH° reacting with reagents of the Fenton reaction.

In tracing the straight line 1/A as a function of the concentration S, the speed constant $k_S$ is determined. The values of the speed constant obtained are:

| Compounds | k Obtained ($10^9 \cdot M^{-1} \cdot s^{-1}$) | Mean k ($10^9 \cdot M^{-1} \cdot s^{-1}$) | Literature k ($10^9 \cdot M^{-1} \cdot s^{-1}$) | No. of Tests |
|---|---|---|---|---|
| Mannitol | 1.52–1.84 | 1.68 | 1.8[15] | 2 |
| Methionine | 5.02–5.36 | 5.19 | 6.5[16] | 2 |
| N-acetyl-methionine | 5.52–5.83–6.70 | 6.02 | 6.7[17] | 3 |
| Minoxidil | 10.20–11.40 | 10.80 | — | 2 |
| Reduced minoxidil | 8.47–9.16 | 8.81 | — | 2 |

| Compounds | k Obtained ($10^9 \cdot M^{-1} \cdot s^{-1}$) | Mean k ($10^9 \cdot M^{-1} \cdot s^{-1}$) | Literature k ($10^9 \cdot M^{-1} \cdot s^{-1}$) | No. of Tests |
|---|---|---|---|---|
| Monosubstituted (N-acetyl-methionine) | 13.10–13.40 | 13.25 | — | 2 |
| Disubstituted (N-acetyl-methionine) | 19.40–19.50 | 19.45 | — | 2 |

The method of production and detection of the hydroxyl radical is validated by comparison of the speed constants obtained with those of the literature (mannitol, methionine and N-acetyl-methionine).

Mannitol is known as being a good sensor of the hydroxyl radical, its speed constant is $1.8.10^9$ $M^{-1}.s^{-1}$.

The new synthesized derivatives have a speed constant greater with respect to mannitol, ranging from five times (reduced minoxidil) to more than eleven times (disubstituted) and a cutaneous penetration substantially greater by more than ten times.

Sensing of hydroxyl radical

The incubation medium is constituted by 2-deoxyribose (0.6 mM), $H_2O_2$ (0.85 mM) and thiobarbituric acid (0.6 mM) in 3 ml of phosphate buffer of pH 7.4 (0.024M $Na_2HPO_4$/$NaH_2PO_4$-0.15M NaCl). The reaction is initiated by the addition of the iron EDTA complex (0.13 mM $(NH_4)_2Fe(SO_4)_2$; 0.143 mM EDTA).

After 15 mins. of incubation at 37° C., the reaction is stopped by the addition of 1.5 ml of cold trichloroacetic acid (TCA) (2.8%).

1 ml of this solution is mixed with 1 ml of thiobarbituric acid (TBA) (1% in 0.05M NaOH) and heated for 15 mins. at 100° C. Then, the specimens are cooled and quantified at 532 nm.

We claim:

1. A compound having one of the following four formulae:

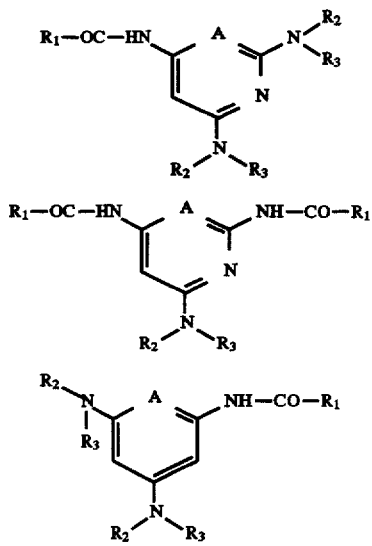

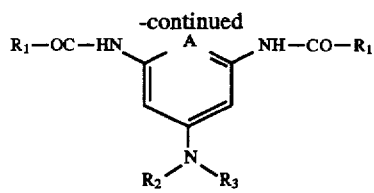

wherein

A is nitrogen or an N-oxide group having the structure $N^+$—$O^-$;

$R_1$ is selected from the group consisting of

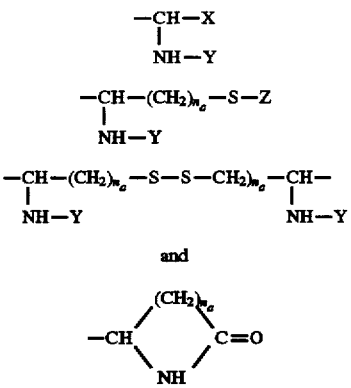

in which X and Y are each independently selected from hydrogen, linear alkyl, branched alkyl, hydroxyl, aryl, alkylaryl, aminoalkyl, aminoaryl, carboxyalkyl, and carboxyaryl, Z is hydrogen, alkyl or aryl, wherein Y may also be CO—$R_4$, $R_4$ being identical to $R_2$ excluding hydrogen, and $n_a$ is an integer from 1 to 6, or wherein —CO—$R_1$ is a peptide residue having two or several amino acids whose acid functions or amino terminals or branchings are free or part of ester or amide groups;

$R_2$ and $R_3$ are each independently selected from hydrogen, linear alkyl, branched alkyl hydroxyl, aryl, amino alkyl, amino aryl, and a heterocyclic moiety, or wherein

is a cyclic structure of the formula

$n_b$ being equal to 4 to 6 or

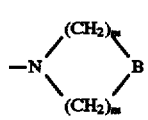

in which m is 2, and B is O, NH, amine substituted by a straight chain alkyl group, a branched chain alkyl group, a hydroxylated straight chain alkyl group, a hydroxylated branched chain alkyl group, or an aryl group;

and mineral or organic salts of said compound.

2. The compound according to claim 1, wherein —CO—$R_1$ comprises at least one amino acid residue selected from the group consisting of glutamic acid, pyroglutamic acid, tyrosine, histidine, arginine, and citrulline.

3. The compound according to claim 1, wherein —CO—$R_1$ comprises at least one amino acid residue selected from the group consisting of methionine, cysteine, S-methylcysteine, S-benzyl-cysteine, cystine, glutathione and oxidized glutathione.

4. The compound according to claim 1, which is a modified minoxidil and wherein —CO—$R_1$ is selected from the group consisting of glutamic acid, pyroglutamic acid, tyrosine, histidine, arginine, and citrulline.

5. The compound according to claim 1, which is a modified minoxidil and wherein —CO—$R_1$ is selected from the group consisting of methionine, cysteine, S-methylcysteine, S-benzyl-cysteine, cystine, glutathione and oxidized glutathione.

6. The compound according to claim 1, which is a monosubstituted or a disubstituted minoxidil derivative.

7. The compound according to claim 1, selected from the group consisting of:
amide of 2,4-diamino-6-piperidinopyrimidine-3-oxide and N-acetyl-D,L-methionine;
diamide of 2,4-diamino-6-piperidinopyrimidine-3-oxide and N-acetyl-D,L-methionine;
amide of 2,6-diamino-4-piperidinopyridine-1-oxide and N-acetyl-D,L-methionine;
diamide of 2,6-diamino-4-piperidinopyridine-1-oxide and N-acetyl-D,L-methionine;
amide of 2,4-diamino-6-piperidinopyrimidine-3-oxide and D,L-methionine;
diamide of 2,4-diamino-6-piperidinopyrimidine-3-oxide and D,L-methionine;
amide of 2,6-diamino-4-piperidinopyridine-1-oxide and D,L-methionine;
diamide of 2,6-diamino-4-piperidinopyridine-1-oxide and D,L-methionine;
amide of 2,4-diamino-6-piperidinopyrimidine-3-oxide and cysteine;
diamide of 2,4-diamino-6-piperidinopyrimidine-3-oxide and cysteine;
amide of 2,6-diamino-4-piperidinopyridine-1-oxide and cysteine;
diamide of 2,6-diamino-4-piperidinopyridine-1-oxide and cysteine;
amide of 2,4-diamino-6-piperidinopyrimidine-3-oxide and cystine;
diamide of 2,4-diamino-6-piperidinopyrimidine-3-oxide and cystine;
amide of 2,6-diamino-4-piperidinopyridine-1-oxide and cystine;
diamide of 2,6-diamino-4-piperidinopyridine-1-oxide and cystine;
amide of 2,4-diamino-6-piperidinopyrimidine-3-oxide and pyroglutamic acid;
diamide of 2,4-diamino-6-piperidinopyrimidine-3-oxide and pyroglutamic acid;
amide of 2,6-diamino-4-piperidinopyridine-1-oxide pyroglutamic acid; and
diamide of 2,6-diamino-4-piperidinopyridine-1-oxide pyroglutamic acid.

8. The compound according to claim 1, selected from the group consisting of:
amide of 2,4-diamino-6-piperidinopyrimidine and N-acetyl-D,L-methionine;
diamide of 2,4-diamino-6-piperidinopyridine and N-acetyl-D,L-methionine;
amide of 2,6-diamino-4-piperidinopyridine and N-acetyl-D,L-methionine;
diamide of 2,6-diamino-4-piperidinopyridine and N-acetyl-D,L-methionine;
amide of 2,4-diamino-6-piperidinopyridine and D,L-methionine;
diamide of 2,4-diamino-6-piperidinopyrimidine and D,L-methionine;
amide of 2,6-diamino-4-piperidinopyridine and D,L-methionine;
diamide of 2,6-diamino-4-piperidinopyridine and D,L-methionine;
amide of 2,4-diamino-6-piperidinopyrimidine and cysteine;
diamide of 2,4-diamino-6-piperidinopyrimidine and cysteine;
amide of 2,6-diamino-4-piperidinopyridine and cysteine;
diamide of 2,6-diamino-4-piperidinopyridine and cysteine;
amide of 2,4-diamino-6-piperidinopyrimidine and cystine;
diamide of 2,4-diamino-6-piperidinopyrimidine and cystine;
amide of 2,6-diamino-4-piperidinopyridine and cystine;
diamide of 2,6-diamino-4-piperidinopyridine and cystine;
amide of 2,4-diamino-6-piperidinopyrimidine and pyroglutamic acid;
diamide of 2,4-diamino-6-piperidinopyrimidine and pyroglutamic acid;
amide of 2,6-diamino-4-piperidinopyridine and pyroglutamic acid; and
diamide of 2,6-diamino-4-piperidinopyridine and pyroglutamic acid.

9. The compound according to claim 1 containing salified aminoalkyl or aminoaryl groups.

10. The compound according to claim 9, wherein said salified aminoalkyl or aminoaryl groups are in the form of a chlorhydrate or an organic or mineral salt of a free carboxylic function.

11. Process for producing a compound of claim 1, comprising reacting an N-substituted amino acid with at least one amino group of an aminopyrimidine or an aminopyridine using a synthetic peptide coupling reagent.

12. Process for producing a compound of claim 1, comprising reacting an N-acetylated amino acid with at least one amino group of an aminopyrimidine or an aminopyridine using dicyclohexylcarbodiimide.

13. Process for producing a compound of claim 1, comprising reacting an N-substituted amino acid with at least one amino group of an aminopyrimidine N-oxide or an aminopyridine N-oxide using a synthetic peptide coupling reagent.

14. Process for producing a compound of claim 1, comprising reacting an N-acetylated amino acid with at least one amino group of an aminopyrimidine N-oxide or an aminopyridine N-oxide using dicyclohexylcarbodiimide.

15. A medicinal composition comprising an antihypertensively effective amount of a compound according to claim 1, in admixture with a pharmaceutically acceptable excipient, and prepared in unit dosage form.

16. A dermopharmaceutical or cosmetological composition comprising an effective amount of a compound according to claim 1 in admixture with a topically acceptable carrier.

* * * * *